(12) United States Patent
Shklyarenko

(10) Patent No.: US 9,072,691 B2
(45) Date of Patent: Jul. 7, 2015

(54) NUTRITIONAL SUPPLEMENT FOR DISINHIBITING THERAPY OF PSYCHIATRIC PATIENTS

(71) Applicant: Liliya Shklyarenko, Boston, MA (US)

(72) Inventor: Liliya Shklyarenko, Boston, MA (US)

( * ) Notice: Subject to any disclaimer, the term of this patent is extended or adjusted under 35 U.S.C. 154(b) by 34 days.

(21) Appl. No.: 13/943,675

(22) Filed: Jul. 16, 2013

(65) Prior Publication Data
US 2014/0023729 A1    Jan. 23, 2014

Related U.S. Application Data

(60) Provisional application No. 61/673,539, filed on Jul. 19, 2012.

(51) Int. Cl.
| | |
|---|---|
| A61K 33/04 | (2006.01) |
| A61K 33/06 | (2006.01) |
| A61K 38/04 | (2006.01) |
| A61K 31/465 | (2006.01) |
| A61K 31/7076 | (2006.01) |
| A61K 31/7004 | (2006.01) |
| A61K 31/355 | (2006.01) |
| A61K 31/10 | (2006.01) |
| A61K 31/185 | (2006.01) |
| A61K 31/197 | (2006.01) |
| A61K 31/455 | (2006.01) |

(52) U.S. Cl.
CPC ............. *A61K 38/043* (2013.01); *A61K 31/10* (2013.01); *A61K 33/06* (2013.01); *A61K 31/465* (2013.01); *A61K 31/7004* (2013.01); *A61K 31/7076* (2013.01); *A61K 31/355* (2013.01); *A61K 31/185* (2013.01); *A61K 31/197* (2013.01); *A61K 31/455* (2013.01)

(58) Field of Classification Search
None
See application file for complete search history.

(56) References Cited

U.S. PATENT DOCUMENTS

2013/0064803 A1*    3/2013    Naidu et al. ................ 424/94.6

* cited by examiner

*Primary Examiner* — H. Sarah Park

(57) ABSTRACT

The present invention is a composition and methods of administering the composition to improve a person's mental and physical health by increasing energy levels, motivation, willingness to communicate, appetite, and memory. The composition may be used to treat mental conditions by improving a person's wiliness and ability to communicate. The increase in appetite effect of the composition may be used to treat eating disorders. The composition comprises a carbohydrate, one or more NAD+/NADP+ producing vitamins, poly-sulfurous chelating agents, vasodilating salts, coenzyme-A producing vitamins, antioxidants, kinins, and biological energy sources.

5 Claims, No Drawings

NUTRITIONAL SUPPLEMENT FOR DISINHIBITING THERAPY OF PSYCHIATRIC PATIENTS

CROSS-REFERENCE TO RELATED APPLICATIONS

This application claims priority to provisional application No. 61/673,539, filed on 19 Jul. 2012, which is fully incorporated by reference.

STATEMENT REGARDING FEDERALLY SPONSORED RESEARCH OR DEVELOPMENT

None

THE NAMES OF THE PARTIES TO A JOINT RESEARCH AGREEMENT

None

BACKGROUND OF THE INVENTION

Current treatments for patients suffering from mental conditions with one or more of the following symptoms: low mental and physical energy level, refusal to eat, loss of ability and will to communicate, decrease in personal hygiene practices and decrease in memory, require using anti-psychotic medications and procedures that are inefficient, costly, traumatic, and have undesirable side effects. Of particular concern are the current treatments of force-feeding patients who have lost the ability to eat, because such procedures terrify the patients and cause them to distrust doctors and clinical personnel.

For patients suffering from the aforementioned conditions, there is a psychiatric need for disinhibiting therapy, which besides improving the person's condition may allow doctors to uncover the symptoms of a mental disease by improving the willingness of a patient to communicate. The existing standard for disinhibition in psychiatric practice was introduced in the United States in 1936 by Samuel Broder (Broder Method). Samuel Broder suggested this method for disinhibiting patients who refused to take food. This method of caffeine-barbamyl disinhibition was widely used in psychiatric clinics in many countries in the world and comprised of the injection of Coffeinum-Natrii Benzoas 1.0-20% subcutaneously, followed by Barbamyl 5.0-10.0% intravenously slowly. The disinhibiting effect lasted 10-15 minutes and the patient had to be closely monitored in order not to miss the beginning of disinhibition. In case of even slight overdose or if the substances were injected too fast, the patient would fall asleep without being able to take food. The Broder Method proved to be not very effective also due to the following flaw—extended use of this method lead to difficulties in feeding patients due to the tolerance that patients would develop towards Barbamyl. The dose of Barbamyl had to be increased to the point that it would become greater than the maximum allowed single dose and thus not possible to inject. Also, it was determined that the repeated injections of Barbamyl lead to psychological and physiological dependency on this substance. Furthermore, the Broder Method does not produce a desirable effect if used only once and the prolonged desired effect is also not observed. In summary, the drawbacks of the Broder Method include: the reliance on the precise timing of the injections, the need for skilled medical personnel to administer the injections, the short duration of the disinhibition effect (only about 15-20 minutes), toxicity issues, and the fact that patients develop tolerance to the treatment over time, decreasing its effectiveness. Despite these shortcomings and the importance of disinhibiting therapy for the treatment of physiological disorders, there has been little progress in developing a successful replacement method for the Broder Method since it was introduced in 1936. Accordingly, a need still exists in the field to provide methods and compositions for a better accomplishing disinhibiting therapy for the treatment of psychological disorders. The present invention provides the composition and technique for an alternative method that disinhibits patients that does not have the flaws of the Broder Method.

In addition to the composition's disinhibiting function, its effect on increasing an individual's appetite may be used as a treatment for eating disorders that is inexpensive, non-toxic, efficient, and does not require specially trained personnel to administer. Patients do not build tolerance to the composition, nor does the composition result in patients developing a physical or psychological dependency.

Eating disorders are wide spread in the United States and are considered a serious social problem, especially among adolescents. The field of psychiatrics is currently lacking an inexpensive and efficient method of treatment of eating disorders.

The individual components of the composition do not have a disinhibiting function or an effect on appetite. It is only through the unique combination of the individual components that the desired effects may be achieved.

BRIEF SUMMARY OF THE INVENTION

The present invention relates to a composition and method to treat low mental and physical energy level, refusal to eat and loss of ability or willingness to communicate in persons suffering from mental conditions, and decrease in memory or concentration performance. Psychological/neurological conditions having such symptoms include, but are not limited to ADHD, autism, catatonia, anorexia, depression, schizophrenia, chronic fatigue syndrome, and certain psychoses. Furthermore, the present invention provides for the use of an active composition for treatment of eating disorders, such as anorexia. One skilled in the art will recognize that there are many additional conditions characterized by these symptoms, beyond what is listed, and the present invention is aimed at these conditions as well.

One embodiment of the invention is a formulation that combines 8 different classes of ingredients, which, when administered together and/or in sequence bring about the alleviation of symptoms associated with certain mental conditions. Such embodiment of the invention comprise a carbohydrate, preferably glucose, one or more NAD+/NADP+ producing vitamins, preferably nicotinic acid or in certain cases nicotinamde, poly-sulfurous chelating agents, preferably Unithiol, vasodilating salt, preferably magnesium sulfate, coenzyme-A synthesis vitamin, antioxidants, kinins and biological energy source as described in detail herein.

Another aspect of the present invention provides a method to disinhibit patients suffering from mental disorders through a series of treatments involving the composition of the invention. This aspect of the invention has an application in psychiatric diagnostics and treatments.

The underlying basis for the invention is the necessity to create a treatment that would be safe for patients, would not have substantial side effects, and would not lose its activity in prolonged use; the kind of treatment that would have a steadily increasing effect with extended use and would not cause allergic reactions.

This treatment would not have effects that would psychologically traumatize patients, and would possess psychologically stimulating and activating effects. Thus, the invention is named "Formula of activity". The invention offers methods of treating patients who refuse food and can die as a result. Since none of the components used had a desired effect on patients if delivered separately from other components of the formula, it is reasonable to suggest that their combination produces a new effect, manifesting in psychological stimulation of patients. It is possible that this new effect is produced by a new substance that is formed as a result of the interaction of the components of the invention with each other or with other naturally occurring substances in the body. The components may exert their effect by through the reticular formation in the brain, which is the regulating center of different brain functions. The reticular formation coordinates the interactions between all structures of the brain. It analyzes and corrects the functions of the brain structures and ensures their proper hierarchical dependencies, as well as the readiness of the central nervous system to perform its functions.

Unless otherwise defined, all technical and scientific terms used herein have the same meaning as commonly understood by one of ordinary skill in the art to which this invention pertains. Suitable methods and materials for practicing the invention are described below, although alternative methods and materials functionally similar or equivalent to those described herein may become evident to one skilled in the art after reading this disclosure, and are also included within the scope of this invention. While there are described herein certain specific embodiments of the present invention, it will be manifest to those skilled in the art that various modifications may be made without departing from the spirit and scope of the underlying inventive concept and that the same is not limited to the particular forms herein described except insofar as indicated by the scope of the appended claims. All publications, patent applications, patents, and other references mentioned herein are incorporated by reference in their entirety. In case of conflict, the present specification, including definitions, will control. In addition, the materials, methods, and examples are illustrative only and are not intended to be limiting.

Other features and advantages of the invention will be apparent from the following detailed description, and from the claims.

DETAILED DESCRIPTION OF THE INVENTION

The following detailed description is provided to enable any person skilled in the art to which the present invention pertains to make and use the same, and sets forth the best mode contemplated by the inventors for carrying out the subject invention.

The invention is a pharmacologically acceptable formulation comprising at least one carbohydrate, one or more NAD+/NADP+ producing vitamins, one or more poly-sulfurous chelating agents, one or more vasodilating salts, one or more coenzyme-A synthesis vitamins, one or more antioxidants, one or more kinins, and one or more biological energy sources, each of which will be detailed further below. Patients do not build tolerance to the composition, nor does the composition result in patients developing a physical and psychological dependency. The individual components of the composition alone do not have a disinhibiting function or an effect on appetite. It is only through the unique combination of each individual component that the desired effects may be achieved. The term "principal active substances" means the active ingredients that are mainly responsible for the pharmacological effect.

Preferably the formulation comprises all those ingredients that are responsible for at least about 75 percent, and more preferably at least about 90 percent of the pharmacological effects. One skilled in the art of formulation would recognize the need to adjust the dosage depending on the route of delivery and biological specifics of the patient so as to achieve the dosage needed to bring about the desired outcome as set forth herein.

As used herein a "pharmacologically acceptable" component is one that is suitable for use in humans without undue adverse side effects such as toxicity, irritation or allergic response, commensurate with a reasonable benefit/risk ratio.

1. A Carbohydrate, Capable of Delivering Additional Energy-Producing Components to Intracellular Metabolic Cycles, and of Adjusting Osmotic Properties of the Invention.

The present invention may comprise at least one carbohydrate ingredient. In a preferred embodiment of the invention, the carbohydrate is glucose in its injectable form (e.g. solution). In each individual case the necessity to deliver the energy-producing components can vary, but usually it is a hypertonic solution of the glucose. Without being bound by theory, it is believed that injecting a hypertonic solution of a carbohydrate stimulates metabolism and improves the action of the invention by providing an immediate source of energy for the metabolic effects accomplished by other ingredients. In a preferred embodiment the dose of glucose is 10 ml of a 40% solution. In some cases, such as when a patient is particularly weak, an isotonic solution of 4.5-5% glucose may be injected at up to 2 liters per day. An alternative way of injecting glucose for patients with concomitant infections is to administer a 5% solution, 100-200 ml or more rectally. A 300 ml solution of glucose may in some cases be administered subcutaneously. In formulations of the invention designed for oral administration, the carbohydrate is preferably solid at room temperature, and may additionally provide bulk "filling" for the oral formulation. In alternative embodiments, and depending on the mechanism of administration, the carbohydrate may be something other than glucose, such as fructose, sucrose, or starch, amongst many other possible carbohydrates. The carbohydrate alone does not provide the effect of the invention unless combined with the other named components of the Composition.

2. A water-soluble vitamin that provides NAD+ and NADP+ to the body.

The present invention may comprise at least one water-soluble NAD+/NADP+ providing vitamin. In a preferred embodiment it is nicotinic acid (niacin, Vitamin B3, Vitamin PP). In alternative preferred embodiments nicotinamide may be used instead of nicotinic acid. Nicotinic acid has two active forms—NAD+ and NADP+, which are electron transporters. They participate in redox reactions and energy metabolism. Nicotinic acid acts as vasodilator for small blood vessels, including blood vessels in the brain. It participates in more than 50 biochemical processes that are involved in the utilization of carbohydrates and lipids for energy, and it also takes part in converting lipids into substances that have hormonal activity, such as eicosanoids. While the NAD+/NADP+ vitamins increase metabolism and some mental functions alone, they do not nearly approach the efficacy of the present invention; it is the synergy of the components of the composition that results in the claimed effects. Without being limited by theory, it is believed that the metabolic and blood flow enhancing qualities of the NAD+/NADP+ producing vitamins enhance the effects of the other components by rapidly delivering them to the brain and body and assisting in metabolizing them. In a preferred embodiment the dose of niacin may be 1 ml of 1% solution, and in alternative embodiments may range approximately between 0.1-5 ml of 0.1-5% solution.

3. A Biological Energy Source that is Necessary for Intracellular Energy Transfer.

The present invention may comprise at least one intracellular energy transfer ingredient. In a preferred embodiment of the invention, the intracellular energy source is adenosine triphosphate (ATP). In other preferred embodiments, other nucleotide triphosphates (alone or mixed) may be used. In yet other preferred embodiments, acetyl phosphate, inorganic polyphosphates, or inosine (an ATP precursor that achieves many of the desired effects of ATP) may be used. Biological phosphates facilitate enzyme activity, act as mediators in the central nervous system, and are involved in creating transmembrane potentials necessary for muscle contraction. In addition to its crucial roles in metabolism, adenosine triphosphate is a neurotransmitter. Long-acting ATP can be used as a supplementary treatment for hypertensive encephalopathy, because of its beneficial effects on cerebral metabolism and its ability to counter the negative effects of hypertension on brain function. Additionally, ATP is used to dilate blood vessels, which provides synergistic effect with other components of the invention. While the biological phosphates are essential for metabolism, when administered alone they do not result in the disinhibitive/appetite promoting effects seen from the inventive composition as a whole. Without being limited by theory, it is believed that the metabolic, vasodilating and neurotransmitter qualities of the biological phosphates both provide immediate energy, and enhance the effects of the other components.

4. A Chelating Agent that has More than One Sulfur Atom in its Chemical Formula.

The present invention may comprise at least one polysulfurous chelating agent ingredient. In a preferred embodiment of the invention, the chelating agent is Unithiol (Dimaval, DMPS). In other alternative embodiments, other sulfhydryl-containing chemicals can be used, such as BAL or DMSA, as well as other chemicals that have metal chelating activity and contain 2 or more sulfur atoms per molecular formula.

Unithiol is a chelating agent that is used as an antidote to heavy metal poisoning, as well as poisoning by cardiac glycosides and alcohol. Its antidote activity is based on the formation of two or more coordinate bonds with a metal ion. The thiol groups in Unithiol form complexes with the heavy metals (bismuth, mercury, chromium, nickel, zinc, antimony, etc.) and the complex is then excreted with urine. As an exemplary effect, DMPS can reverse the effects of severe mercury vapor-induced neurological damage. Unithiol does not affect the metabolism of biometals, nor does it have a recorded history of use in psychiatric practice prior to use in the present invention. When used as a part of this composition, it is believed that the chelating agent enhances the action of calcium pantothenate and quickly neutralizes the adverse effects of acetaldehyde, in addition to removing harmful heavy metals that may be affecting the nervous system. For Unithiol, in a preferred embodiment the dose may be 5 ml of 5% solution, and in alternative embodiments the dose is calculated, considering the maximum dose of 0.05 gram per 10 kg of body weight. Unithiol is not a neuroleptic or an antidepressant, or a tranquilizer. If administered separately from the other components of the invention, it does not lead to a desired stimulating or disinhibiting effect.

5. A Salt that Produces Peripheral Vasolidation, Decreases the Liberation of Acetylcholine in the Nerve Endings, and Decreases the Blood Pressure.

The present invention may comprise at least one salt that produces peripheral vasolidation, decreases the liberation of acetylcholine in the nerve endings, and decreases the blood pressure as an ingredient. In a preferred embodiment of the invention, it is magnesium sulfate (Epsom salt).

Magnesium sulfate, when administered parenterally without the other components of the present invention, has a sedative effect on the central nervous system. It helps to decrease the activity of the respiratory center, to lower high blood pressure, and is used as an electrolyte replenisher.

Magnesium sulfate for women with eclampsia reduces the risk ratio of maternal death and of recurrence of seizures, compared with diazepam. Antenatal magnesium sulfate can be given to improve neonatal neurological outcome in clinical practice, reducing or preventing cerebral palsy. These neurological effects are completely separate from the effects noted in the current invention. In certain embodiments of the present invention that are administered orally, the use of magnesium sulfate may be excluded, as oral adminitration of magnesium sulfate has a laxative effect. In a preferred embodiment of the invention involving non-oral administration, the dose of magnesium sulfate may be 3.5 ml of 25% solution, and in alternative embodiments it may be a 4% to 30% solution, the total dose is determined according to the patient's response to the blood pressure decrease. Magnesium sulfate alone is not a neuroleptic or an antidepressant, or a tranquilizer. If administered separately from the other components of the invention, it does not lead to a desired stimulating or disinhibiting effect. Without being bound by theory, it is believed that the vasodilating and blood pressure reducing effects of the salt help to increase the blood flow to the brain and other organs and tissues, helping to deliver other ingredients of the invention, and thereby increasing mental functions and providing greater access to stored and administered metabolic energy sources.

6. A Water-Soluble Vitamin or its Derivative that Participates in the Synthesis of Coenzyme A.

The present invention may comprise at least one water-soluble vitamin or its derivative that participates in the synthesis of coenzyme A as an ingredient. In a preferred embodiment of the invention, it is calcium pantothenate (Vitamin B5). In alternative embodiments other derivatives of pantothenic acid or pantothenic acid itself can be used.

After it is absorbed in the intestine, vitamin B5 is broken down to form pantothenic acid (also called pantothenate), which is required for the synthesis of coenzyme A, an important molecule in energy metabolism. Pantothenate is involved in metabolism of carbohydrates, lipids, and speeds up tissue regeneration processes. Pantothenate also is required for the synthesis of steroid hormones and improves the contractile function of the heart muscle. Indications for use are: neuropathies, neurasthenia, and abstinent syndrome in alcoholism. It is incorporated into coenzyme A and protects cells against peroxidative damage by increasing the level of glutathione. Calcium pantothenate is not a neuroleptic, an antidepressant, or a tranquilizer. In a preferred embodiment, calcium pantothenate may be administered in the dose of 2 ml of a 20% solution, and in alternative embodiments the dose may be a 5% to 30% solution to the total of 200-400 mg. Without being limited by theory, it is believed that calcium pantothenate may participate in providing the desired effect of the invention by enhancing different parts of the carbohydrate, lipid and energy metabolic processes and by protecting cells from oxidative damage. If administered separately from the other components of the invention, it does not lead to a desired stimulating or disinhibiting effect.

7. Antioxidants.

The present invention may comprise at least one antioxidant as an ingredient. In a preferred embodiment of the invention the antioxidant is Vitamin E. Antioxidants are biologically active substances that can be either natural or chemically synthesized. They reduce the activity of the processes that involve oxidation by free radicals. Indications for use of antioxidants include different types of diseases and pathological conditions in which oxidation by free radicals is a part of pathogenesis; this includes psychiatric and neurological conditions. Excessive production of free radicals can be caused by psychological stress, neurological and psychiatric disorders, physical and emotional overload. Antioxidants bind free radicals and remove them from biochemical processes, thus protecting the organism from damage.

Antioxidants comprise several classes of compounds that are found in plants, chemically synthesized, or belong to a group of microelements. Vitamin E is a natural fat-soluble vitamin that possesses antioxidant activity and in a preferred embodiment is administered intramuscularly as alfa-tocopherol 1 ml of 5%-10% solution. In alternative embodiments, vitamin E is administered orally in the amount of 7 mg to 30 mg of alfa-tocopherol per day, the average of 15 mg (22.4 IU)/day, where IU is international units.

In alternative embodiments of the invention, dihydroquercetin, selenium, acai extract, and other natural or synthetic substances with similar known antioxidative activity can be used as the antioxidant ingredient. Without being limited by theory, it is believed that antioxidants positively contribute to the effects of the invention by providing protection to cells from damage caused by the by-products of the changed/increased metabolism, and by removing free radicals caused by psychological and other stresses. Taken alone, antioxidants do not provide the effects of the invention.

8. Kinins.

The present invention may comprise at least one kinin as an ingredient. In a preferred embodiment of the invention bradykinin is the kinin used Kinins are also called tissue hormones. Without being limited by theory, their functions that are believed to positively contribute to the effects of the invention are vasodilation and anti-spasm activity that leads to improvement in blood circulation and decrease in the blood pressure, as well as an increase in the speed of the blood flow, which improves blood supply to tissues and organs. Also, one of the potential mechanisms by which kinins can positively contribute to the desired effects of the present invention is the release of NO (nitric oxide) in tissues. Bradykinin in a preferred embodiment of the present invention is administered intravenously, 30 ng/kg of body weight for 2 hours, and in alternative embodiments from 200 pg/kg of body weight for 2 hours to 60 ng/kg of body weight for 2 hours, or orally 0.2-0.5 mg per day for up to 2 weeks. In alternative embodiments of the invention, the biologically active kinins neuropeptides A and B, and/or Substance P may be used. These kinins relax the smooth muscles of the peripheral blood vessels, which improves blood circulation and increases the blood flow and positively affects the delivery and activity of the other components of the invention and thus helps to achieve the goal of disinhibition and stimulation. Other effect of the kinins that may positively affect the action of the invention is their stimulation of the activity of antioxidant intracellular molecules.

Composition

A preferred composition of the present invention is a formulation of eight essential components preferably in quantities set forth below in Table 1.

TABLE 1

| Composition | Dosage | Alternative dosage |
|---|---|---|
| Glucose | 10 ml of 40% solution (4 g) parenterally | 100-200 mL of 5% solution intravenously<br>100-200 mL of 5% solution rectally<br>300 mL of 5% solutions subcutaneously |
| Nicotinic acid | 1 ml of 1% solution (10 mg) parenterally | 0.1 to 5 mL of 0.1-5% solution parenterally |
| ATP | 2 ml of 1% solution (20 mg) parenterally | 1-6 ml of 0.5-2% solution parenterally |
| Unithiol | 5 ml of 5% solution (250 mg) parenterally | Up to the maximum of 0.05 gram per 10 kg of body weight |
| Magnesium sulfate | 3.5 ml of 25% solution (850 mg) parenterally | 4-30% solution, amount determined by patient's response |
| Calcium pantothenate | 2 ml of a 20% solution (400 mg) parenterally | 5-30% solution, the total amount of 200-400 mg parenterally |
| Vitamin E in the form of alpha-tocopherol | 1 ml of 5%-10% solution intramuscularly. | From 7 mg (10 IU) to 30 mg (44.8 IU)/day orally, average dose 15 mg (22.4 IU)/day orally. |
| Bradykinin | 30 ng/kg of body weight per minute for 2 hours intravenously | From 200 pmol/kg of body weight intravenously per minute for 2-4 hours to 60 ng/kg of body weight per minute for 2 hours intravenously;<br>Orally - 0.2-0.5 mg per day for up to 2 weeks |

The preferred embodiment of the composition in an injectable form comprises: 1) Unithiol, delivered as 5 ml of a 5% solution, 2) magnesium sulfate as 3.5 ml of a 25% solution, 3) nicotinic acid as 1 ml of 1% solution, 4) calcium pantothenate as 2 ml of 20% solution, 5) adenosine triphosphoric acid as 2 ml of 1% solution, 6) bradykinin, the total injected dose calculated as 30 ng/kg of body weight for 2 hours of intravenous infusion, 7) vitamin E is administered as alfa-tocopherol 1 ml of 5%-10% solution intramuscularly. Concentrations are weight/volume with water as the solvent. The preferred sequence of delivery of the components begins with intramuscular injection of 5 ml of 5% Unithiol (250 mg), followed by intramuscular injection of 3.5 ml of 25% magnesium sulfate (850 mg), followed by slow intravenous injection of 1 ml of 1% nicotinic acid (10 mg) and then 10 ml of 40% glucose (4 g). Without removing the needle from the vein, using another syringe the following composition is administered: glucose 40%-10 ml (4 g), calcium pantothenate 2 ml of 20% (400 mg) and adenosine triphosphate 2 ml of 1% (20 mg), followed by the infusion of bradykinin in the dose of 30 ng/kg of body weight for 2 hours, and then vitamin E is administered intramuscularly as alfa-tocopherol, 1 ml of 5%-10% solution.

Varied concentrations and amounts may be used in alternative embodiments. For example, the dose of Unithiol is calculated considering the maximum dose of about 0.05 gram per 10 kg of body weight. For magnesium sulfate, concentrations may vary between about 4 and 30%, where the total dose is determined according to the patient's psychological response and decrease in blood pressure. For nicotinic acid, the concentration may be about 0.1-5% and the total volume about 0.1-5 ml. For glucose, the concentration may be about 5-40%, and the total volume administered may be between about 100 ml-2 L. For a carbohydrate (such as glucose) the amount may be up to about 15 g per single dose, and it is generally understood that a carbohydrate (such as glucose) would have to be dosed more liberally than other active ingredients of the formulation, and in the case of disorders of carbohydrate metabolism such as diabetes, may be eliminated from the formulation or decreased as needed. For calcium pantothenate, the concentration may be about 5% to 30% solution with a total amount administered between about 200-400 mg. For ATP, the concentration may be between about 0.5-2% and the total volume administered may be between about 1 ml and 6 ml. For bradykinin, the lower effective dosage is calculated as about 200 pg/kg of body weight for 2 hours of intravenous infusion up to about 60 ng/kg of body weight of intravenous infusion for 2 hours. Vitamin E is never administered intravenously, and in the preferred embodiment the only parenteral administration is either intramuscular or another way of parenteral delivery that excludes the possibility of vitamin E being delivered into the bloodstream. Parenteral delivery of about 1 ml of 5%-10% of vitamin E could be done less frequently than every day, in order to avoid excess amount being absorbed into the body, while oral administration of smaller doses of vitamin E of up to about 30 mg (44.8 IU) can be done daily (where IU is international units). Percent concentrations are given as weight/volume and the solvent is water or physiological salt solution, such as saline. The upper limit is imposed by concern over side effects rather than a loss of efficacy.

Alternative preferred embodiments of the invention provide for the formulation to be administered orally, in the form of tablets, capsules, or other compact forms that can be easily swallowed and/or absorbed, such as lacquered tablets, unlacquered tablets, caplets or capsules referred to simply as tablets without distinction in form or function, herein. This may take the form of separate tablets for each of the components administered in a sequence similar to that used in injectable forms, or as a combination of all ingredients combined together into one tablet, given that an oral formulation may exclude the use of magnesium sulfate.

The regimen of taking the mixture orally may differ depending on the particular state of health of a person who would be taking it, and on the desired strength of the effect. Different vehicles for the delivery of active ingredients of the invention may be used; the choice of each particular vehicle is dependent upon the choice of an embodiment of the invention (swallowed tablets, sublingual tablets, a liquid solution, nasal spray, a film for attaching to epithelial surfaces, etc.).

Alternative embodiments may consist of a combination of intravenous/intramuscular injection of a mixture of some of the components (particularly magnesium sulfate) and oral administration of some other components where magnesium sulfate may be needed to achieve full result.

The percentages of components and the choice of components used for the oral form of the invention may vary depending on the stability and desired strength of the composition, and different components that are present in one preferred or alternative embodiments may be changed in other embodiments such that they provide a similar chemical and biological action according to each individual's physiological and psychological conditions. The amounts of the various components to be used in a particular embodiment based on the above criteria will be immediately apparent to one skilled in the art of tablet design and manufacturing. In persons with more pronounced and acute conditions, especially in persons who require hospitalization or are already hospitalized, a faster effect may be needed, and it might call for the choice of parenteral administration of the formulation over other forms of administration. In persons with more chronic and mild conditions, especially those who do not require hospitalization or refuse hospitalization, the oral formulation and method of delivery may be chosen. Also, depending on concurrent pathology, such as diseases of the gastrointestinal tract, methods of administration can be chosen that are different from oral or injectable, such as inhalation sprays, sublingual tablets, etc. In cases where dosages of the components would have to be adjusted by the person skilled in the art, it may require administering all or some of the components separately from the rest of the components. The strength of the desired effect may necessitate following a similar scenario, where one skilled in the art would reduce the doses of some components, but not the others.

Tablet-based embodiments of the subject composition may contain larger quantities of essential ingredients per tablet than the minimum quantities specified in Table 1. The minimum quantities specified reflect the minimum amount of each essential ingredient to be finally delivered after digestion, through to the date of tablet expiration as set forth on the tablet sale label. However, since essential ingredients are subject to degradation over time, and some ingredients will be lost in digestion, the tablets may contain larger quantities of essential ingredients to compensate for ingredient loss. Another consideration in formulating the subject composition is that, depending on the source of the individual ingredients, individual ingredient degradation rates may vary. For example, depending on the source of vitamin E, an extra quantity of approximately 10 percent to an extra quantity of approximately 60 percent more Vitamin E may be necessary per tablet to provide the specified amount of Vitamin E per tablet as that listed on the tablet sales-label through to the expiration date of the product. Accordingly, the specific formulation of the subject composition will vary depending on the sources of the individual ingredients and the specified length of product shelf life before expiration. Typically, the product shelf life for psychiatric treatments is two to three years. Tablet formulations may also vary somewhat depending on slight deviations from manufacturing specifications within controlled tolerance ranges as is customary within the field of art.

The essential ingredients of the subject composition, as well as any desired inactive ingredients and/or additive ingredients/stabilizers may be combined by weight as described above and combined, such as for example, through the use of a blender to form a blend. If necessary, the blend is then mixed until uniform. The blend is then compressed using a tablet press to form tablets. Optionally a coating may be sprayed on the tablets and the tablets tumbled until dry. Alternatively, the blend may be placed in mineral oil to form a slurry for containment in a soft gel capsule, the blend may be placed in a gelatin capsule or the blend may be placed in other dosage forms known to those skilled in the art.

Variations contemplated in administering the subject composition as a tablet include, but are not limited to, providing time-release tablets or tablets manufactured to be administered as a single dose or as other multiple part dosages. Additionally, alternative avenues of administration besides oral and intravenous administration are contemplated herein such as for example, but not limited to, intraperitoneal, subcutaneous, sublingual, transcutaneous, intramuscular or like forms of administration. Each tablet of the subject composition preferably contains the essential ingredients in the quantities specified, including overages to compensate for ingredient degradation/digestive loss. For purposes of simplicity only, formulations of the subject composition are provided below in accordance with a one-tablet, oral daily dosage regime.

The preferred daily dosage of the subject composition as specified above may be administered in the form of 1 tablet of active ingredients plus filler per day. In a preferred method of administration, the daily dosage of the subject composition is provided in the form of one tablet for the first three days followed by one tablet every third day for a total of 10 tablets, or in the form of one tablet taken twice daily, for a total of two half-dose tablets a day. Compared to taking the total daily dose once a day, twice daily dosing of half the total daily dose in one or more tablets per dose may provide improved absorption and better maintenance of blood levels of the essential ingredients.

Accordingly, if one tablet of the preferred formulation of the subject composition is to be ingested each day, each tablet may be formulated to preferably provide not less than approximately 250 mg of Unithiol, approximately 15 IU of alpha-tocopherol, approximately 10 mg of nicotinic acid, approximately 4 g of glucose or other suitable carbohydrate, approximately 400 mg of calcium pantothenate, approximately 20 mg of adenosine triphosphate, and approximately 0.25 mg of bradykinin upon oral administration. If two tablets of the preferred formulation of the subject composition are to be ingested each day, each tablet is formulated to preferably provide not less than approximately 125 mg of Unithiol, approximately 7.5 IU alpha tocopherol, approximately 5 mg of nicotinic acid, approximately 2 g of glucose, approximately 200 mg of calcium pantothenate, approximately 10 mg of adenosine triphosphate, and approximately 0.125 mg of bradykinin upon oral administration. Alternatively, the same dosages may be provided in liquid oral form, where the filler liquid is provided in such a way that administering the liquid oral form by one teaspoonful would be an equivalent of administering one tablet described above. Additionally, subcutaneous administration would take into account the absorptivity of the ingredients and the need to provide a different dosage per subcutaneous injection than for intravenous and/or intramuscular. The single dose administered as a subcutaneous injection would on average provide the same amounts of the active ingredients as one tablet.

Alternative embodiments may consist of all the ingredients combined administered in a single dose, or in multiple administration of smaller doses over a length of time required to bring about a similar outcome as outlined herein.

TABLE 2

Efficacy of a preferred embodiment of claimed composition for patients with varied diagnoses.

| Diagnosis | Number of patients | Outcome without improvement | Improvement while in the hospital* | Improvement with discharge from the hospital** | Stable remission/recovery*** |
|---|---|---|---|---|---|
| Schizophrenia | 64 | 5 | 20 | 32 | 7 |
| Atherosclerosis of the cerebral arteries with pronounced asthenic-neurotic syndrome and different degrees of memory capacity reduction | 17 | 0 | 4 | 7 | 6 |
| Hyposthenic form of neurasthenia | 13 | 0 | 0 | 5 | 8 |
| Chronic fatigue syndrome | 12 | 0 | 0 | 4 | 8 |
| Organic psychoses | 14 | 1 | 3 | 7 | 3 |
| Endocrine diseases with astheno-abulic syndrome | 3 | 0 | 0 | 2 | 1 |
| Reactive psychoses | 9 | 0 | 0 | 0 | 9 |
| Postpartum psychoses | 1 | 0 | 0 | 0 | 1 |
| Post-infectious psychosis related to flu | 2 | 0 | 0 | 1 | 1 |
| Closed head trauma | 1 | 0 | 1 | 1 | 1 |

Comments:
*This group comprises patients who remained in the hospital after the end of treatment since they had no family or relatives and could not be discharged from the hospital for that reason.
**This group comprises patients who began behaving adequately and were able to take care of themselves fully; some of them lived by themselves.
***This group comprises patients who returned to productive work, unless there were age restrictions.

Effect of Composition on Selected Patients and Disorders

The following are several of many patients who were successfully treated by the invention.
Patients are grouped according to the diagnoses presented in Table 2.
Schizophrenia.

Patient N, a 43 year old male. Hospitalized for more than 25 years, has no relatives. Diagnosis: Simple form of schizophrenia. This patient suffered from the apathy abulia defect. Contact with him could not be established, as he wouldn't answer questions. He followed the personnel's instructions with difficulty and was not involved in labor. He would dress with the help of the personnel and ate by himself, but was very untidy. This patient was treated with the invention via injections every third day for a total of 15 injections, and after a 30-day break he received an additional 10 injections every other day. After this treatment, Mr. N's condition changed noticeably. He was able to find his own clothes among other patients' items, was eager to work in the shop on the hospital's premises and started to work in the mattress department (installing the mattress filling). He also began to help cleaning the premises and assisted the hospital workers in gathering up the other patients and taking them to a labor department. He answered questions correctly, in one or two words, and he didn't feel burdened by staying in the hospital.

Patient A, a 38 year old female and an inpatient for more than 5 years. Diagnosis—catatonic schizophrenia. For many years this patient would get liquid food through a tube against her will. The year before the treatment started, she would get food through disinhibiting via the Broder Method. It was not always possible to feed the patient, because she often fell asleep. Most of the time the patient was exhausted and stayed in bed with her head slightly elevated (air pillow syndrome), had no reaction to speech directed towards her, wouldn't follow instructions, fought feeding and was untidy. The invention was administered via injections every other day for a total of 20 days. From the first day of treatment it became possible to feed the patient with a spoon, and she started to get up from bed. She took care of her personal hygiene, and answered questions correctly in one or two words. Clinical personnel were able to stay in contact with her for 2-5 hours following the treatment. By the end of the treatment patient A became more energetic. She was still sluggish, but tried to eat by herself, became more organized, and took showers with the help of the personnel. Personnel were able to engage in simple active contact with her which would last for 2 to 5 hours after the injections.

Patient B, a 27 year old male. Diagnosis—paranoid schizophrenia with hallucinations. The patient was admitted to a psychiatric ward for the first time in his life. According to his relatives, there was no family history of mental illness. The patient worked as a sailor on a freight ship. The medical history of the patient included a fall with a loss of consciousness and subsequent hospitalization to a neurological department of a hospital where he stayed for 2.5 months. The condition of the patient upon admission to a psychiatric ward was: sitting in one position, not reacting to the words addressed to him, not following instructions, and making no eye contact. No overt signs of hallucinations or delusions. Diagnosis at admission: simple form of schizophrenia. The patient was administered the invention with the subsequent effect of disinhibition that manifested itself in pronounced behavioral change. The patient started shouting at the personnel, using insulting words, visibly tried to listen to something, expressed delusional ideas of reference and paranoid ideas of persecution. After administration of 50 mg of aminazine intravenously, the patient fell asleep. This case emphasizes the application of the invention in psychiatric diagnostics. Prior to using the invention, the correct diagnosis was impossible to determine due to the lack of clinical signs. Disinhibition revealed the hallucination-delusion syndrome and aggressiveness. The patient received the treatment aimed at prevention of the aggressive behavior and alleviating hallucination-delusion syndrome. Only after administering the invention and subsequent disinhibition of the patient, did the symptoms of a more complex nature manifested. From these symptoms, a correct diagnosis was determined and adequate treatment was administered.

Atherosclerosis of the Cerebral Arteries with Pronounced Asthenic-Neurotic Syndrome and Different Degrees of Memory Capacity Reduction.

Patient M, a 65 year old male, an outpatient. Diagnosis: brain arteriosclerosis, neurasthenic stage. This patient noted: partial memory loss of current events, sluggishness, reduction of interests, physical weakness, and impotency. After the treatment was given to him in accordance with the claimed composition and method, every third day for a total of 12 days, the patient showed the following improvements: he became more active, started to smile, became friendly and interested in getting new information, noted memory recovery and elevated potency. Six months after the treatment patient M "felt good."

Patient K, a 69 year old male. Diagnosis at admission: atherosclerosis of cerebral blood vessels. Pronounced hyposthenic form of neurasthenia. The patient had difficulty coping with his retirement, and he began to express feelings that his life was pointless. He felt tired, apathetic, and experienced short term memory loss. Patient K lost interest in life and stopped communicating with relatives and friends. In a conversation with the patient he appeared sluggish, not willing to answer the questions, but for the few questions he did provide answers that were brief and to the point. He was treated as an outpatient, visiting the doctor accompanied by relatives. The invention was used to treat him, the total of 10 doses administered every third day. His condition gradually improved, he started to visit the doctor by himself without being accompanied by anyone. He became more active in a conversation, friendly and smiling, and became interested in going to another city to visit his brother. Exhibiting some embarrassment, he shared that he "became a man again". He started to visit his former place of employment, where he was asked to help with training younger employees, which he became eagerly engaged in. At the same time he noted that "it's time to rest". He underwent an additional course of therapy with the invention for a total of 6 doses two times a week. Upon completion of the course, he informed us that he intends to buy a small piece of land outside of town and grow some vegetables and flowers. The patient completely recovered and the treatment was discontinued.

Postpartum Psychoses.

Patient N. Diagnosis: postpartum psychosis. The patient became sick after giving birth. Labor was without complications and the child was normal. On day 8-10 after giving birth, the patient developed apathy, adynamia, torpitude, delusional ideas of reference, delusionally interpreted her husband's anxiety regarding her condition, and was not interested in the condition of her newborn child. The patient was kept in a psychiatric unit, her husband was visiting her to provide help, but the patient showed reluctance to follow the necessary procedures, and was taking food only from the personnel. The general physical condition of the patient remained satisfactory. Stelazine was administered in a dose of 5 mg once per day during the first week, and after that 1 mg two times a day. The patient improved regarding her condition and delusional ideas; however she remained apathetic, fatigued and indifferent. She was taken off stelazine and the invention was administered 10 times every day for three days, and then 7 times every third day. After the course of treatment was completed, the condition of the patient improved significantly. She became active and fully aware of the delusional nature of her ideas at the onset of the disease. She was discharged from the hospital but continued her outpatient visits to the hospital once per week to have the invention administered for the period of two months.

Closed Head Trauma.

Patient S, a 52 year old male. Diagnosis at admission: contusion of the brain, medium severity, due to a closed head injury. The patient fell from the ladder while fixing the roof (second floor level). Symptoms included: loss of consciousness for up to 20-25 minutes, headache, dizziness, nausea, vomiting, retrograde and anterograde amnesia. Physical status: AD 165/85 (130/75 before trauma), tachycardia. Neurological status: syndrome of brain contusion, meningeal signs—Babinski's and Kernig's signs, as well as signs of contusion of lumbar and sacral plexuses. The patient received the following treatment: intravenously magnesium sulfate, vitamins of B group, nicotinic acid and glucose. On the seventh day of the treatment the condition of the patient improved greatly, headache disappeared, nausea and dizziness went away. Patient was lucid, with somewhat reduced activity in verbal contact, memory partially restored. Physical activity was limited, the patient was sluggish, moving around the ward accompanied and supported by the personnel. He quickly fatigued and became sleepy; however he would fall asleep only after injection of valium. Interests of the patient were limited. A course of the injections of the invention was administered, totaling 10 doses every third day. During the injection of the invention the patient became more active and more willing to take food. After the fifth injection of the invention he began to actively engage in contact with the personnel, remembered their names, and asked to increase the time of walking. However he still would get tired quickly and mild dizziness appeared. At the end of the course of treatment the patient was lucid, his memory restored, he adequately reacted to what happened to him and expressed regret over not fixing the roof as a result of the accident. He was discharged in the satisfactory condition, his condition to be further monitored by a neurologist.

Chronic Fatigue Syndrome.

Patient S, a 45 year old female. Diagnosis: Chronic fatigue syndrome. Evaluation: neurocirculatory dystonia. The patient complained of constant fatigue that appeared when she was about 30 years old. At the age of 21 she had a complicated labor, and gave birth to a healthy child. She used to work at a factory with a high noise level, but for the last 8 years she worked in a quiet environment. She was given a course of injection therapy with vitamins of B group and vitamin C, together with periods of rest, but that did not improve her condition. The patient was administered physical therapy and special exercise therapy, together with 10 doses of the invention. The first 3 injections of the invention were given every other day, the remaining 7 were given every third day. The condition of the patient began to improve after the fifth injection. At the end of treatment with the invention she became more active and alert, the feeling of fatigue went away, and the patient returned to active work.

We claim:

1. A mixture to alleviate conditions that are characterized by low energy, fatigue, exhaustion, or lack of concentration, comprising therapeutically effective amounts of each of at least one carbohydrate, one or more water-soluble NAD+/NADP+ providing vitamins, one or more organic phosphates or its precursors, one or more metal chelating agents, one or more vasodilating agents, one or more antioxidants, and one or more kinins;
    wherein the one or more carbohydrate is glucose, sucrose, fructose, or another mono- or di-saccharide, the one or more organic phosphate comprises adenosine triphosphate or acetyl phosphate, the one or more metal chelating agent comprises unithiol or another sulfhydryl-containing chelating agent, the vasodilating agent is magnesium sulfate, and the one or more kinins comprise bradykinin, substance P, and neurokinin; and
    wherein the mixture additionally comprises pantothenic acid or a metal salt of pantothenic acid.

2. A method of treating a neurological or psychological condition comprising administering the mixture of claim 1 to a patient suffering from said neurological or psychological condition.

3. The method of delivery of the mixture of claim 1 comprising intravenous, intramuscular, or subcutaneous injections, oral administration, transdermal or transepithelial administration in the form of ointment, lotion, cream, sublingual form, nasal drops, rectal suppositories, or spray inhalation mixture.

4. A method for the delivery of the mixture of claim 1 that comprises the following sequences of actions: intramuscular injection of about 5 ml of 5% Unithiol (250 mg), followed by intramuscular injection of about 3.5 ml of 25% magnesium sulfate (850 mg), followed by slow intravenous injection of about 1 ml of 1% nicotinic acid (10 mg) and then about 10 ml of 40% glucose (4 g); followed by administering about 40%-10 ml (4 g) of glucose, about 2 ml of 20% (400 mg) of calcium pantothenate and about 2 ml of 1% (20 mg) of adenosine triphosphate, followed by the infusion of bradykinin in the dose of about 30 ng/kg of body weight for 2 hours, and administering 1 ml of 5%-10% solution of vitamin E intramuscularly.

5. A method of delivering the mixture of claim 1 wherein the mixture comprises approximately 250 mg of unithiol, approximately 15 IU of vitamin E (alpha tocopherol), approximately 10 mg of nicotinic acid, approximately 4 g of glucose or another mono- or di-saccharide, approximately 400 mg of calcium pantothenate, approximately 20 mg of adenosine triphosphate, and approximately 0.25 mg of bradykinin.

* * * * *